(12) United States Patent
Alvarez et al.

(10) Patent No.: US 10,335,342 B2
(45) Date of Patent: Jul. 2, 2019

(54) METHOD, SYSTEM, AND APPARATUS FOR TREATMENT OF BINOCULAR DYSFUNCTIONS

(71) Applicant: New Jersey Institute of Technology, Newark, NJ (US)

(72) Inventors: Tara Lynn Alvarez, Whippany, NJ (US); John Vito D'Antonio-Bertagnolli, Mount Laurel, NJ (US); Robert Gioia, Copiagne, NY (US); Mitchell Scheiman, Bala Cynwyd, PA (US); Chang Yaramothu, Hackensack, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

(21) Appl. No.: 15/746,757

(22) PCT Filed: Jul. 22, 2016

(86) PCT No.: PCT/US2016/043673
§ 371 (c)(1),
(2) Date: Jan. 22, 2018

(87) PCT Pub. No.: WO2017/015603
PCT Pub. Date: Jan. 26, 2017

(65) Prior Publication Data
US 2018/0214338 A1  Aug. 2, 2018

Related U.S. Application Data

(60) Provisional application No. 62/195,864, filed on Jul. 23, 2015.

(51) Int. Cl.
*A61B 3/08* (2006.01)
*A61H 5/00* (2006.01)
(Continued)

(52) U.S. Cl.
CPC ............... *A61H 5/00* (2013.01); *A61B 3/08* (2013.01); *A61B 3/113* (2013.01); *A63F 13/213* (2014.09);
(Continued)

(58) Field of Classification Search
CPC .. A61H 5/00; A61H 5/005; A61H 2201/5007; A61H 2201/5043; A61H 2201/5092
(Continued)

(56) References Cited

U.S. PATENT DOCUMENTS 5,293,187 A  3/1994 Knapp et al.
7,616,125 B2  11/2009 Johns
(Continued)

OTHER PUBLICATIONS

Blaha, James, Announcing the Clinical Beta for Vivid Vision for Amblyopia, Vivid Vision, May 25, 2018.
(Continued)

*Primary Examiner* — Mohammed A Hasan
(74) *Attorney, Agent, or Firm* — McCarter & English, LLP

(57) ABSTRACT

Exemplary embodiments of the present disclosure relate to systems, methods, and apparatus for vision therapy. In exemplary embodiments a visual therapy game can be rendered on one or more displays and the visual therapy game can be controlled by eye movements of the user. Visual stimuli incorporated in the visual therapy game can be rendered to facilitate vergence eye movements for the treatment of binocular dysfunctions.

18 Claims, 9 Drawing Sheets

(51) Int. Cl.
*A61B 3/113* (2006.01)
*A63F 13/213* (2014.01)

(52) U.S. Cl.
CPC .............. *A61H 2201/5015* (2013.01); *A63F 2300/8094* (2013.01)

(58) Field of Classification Search
USPC ....................................................... 351/203
See application file for complete search history.

(56) References Cited

U.S. PATENT DOCUMENTS

| | | | |
|---|---|---|---|
| 8,066,372 | B2 | 11/2011 | Cooperstock et al. |
| 8,807,749 | B2 | 8/2014 | Fateh |
| 9,706,910 | B1 | 7/2017 | Blaha et al. |
| 9,788,714 | B2 | 10/2017 | Krueger |
| 2011/0075257 | A1 | 3/2011 | Hua et al. |
| 2012/0179076 | A1 | 7/2012 | Bavelier et al. |
| 2012/0307203 | A1* | 12/2012 | Vendel ................ A61B 3/085 351/201 |
| 2014/0192316 | A1* | 7/2014 | Krenik ................ A61B 3/032 351/203 |
| 2014/0320808 | A1* | 10/2014 | Kiderman ............ A61B 3/145 351/206 |
| 2017/0000331 | A1 | 1/2017 | Samec et al. |
| 2017/0293356 | A1 | 10/2017 | Khaderi et al. |
| 2018/0008141 | A1 | 1/2018 | Krueger |
| 2018/0084232 | A1 | 3/2018 | Belenkii et al. |

OTHER PUBLICATIONS

International Search Report and Written Opinion from related International Patent Application No. PCT/US2016/043673 dated Oct. 6, 2016.
(SINHA. 5) "VR Helps Treat Poor Vision" in EE Times, Wireless & Networking. Jul. 20, 2016.
PCT/US2016/043673, Jul. 22, 2016, WO 2017/015603.
U.S. Appl. No. 62/195,864, filed Jul. 23, 2015.
Kotulak, et al., The Effects of Optical Vergence, Contrast, and Luminance on the Accommodative Response to Spatial Bandpass Filtered Targets, Vision Research, vol. 27, Issue 10, pp. 1797-1806, 1987. 12 Pages.
Duchowski et al., Binocular Eye Tracking in VR for Visual Inspection Training, Proceedings of the ACM Symposium on Virtual Reality Software and Technology, ACM, 2001, 8 pages.
Duchoweki et al., 3D Eye Movement Analysis for VR Visual Inspection Training, Proceedings of the 2002 Symposium on Eye Tracking Research & Applications, ACM, 2002, 8 pages.
Scheiman, et al., Treatment of Convergence Insufficiency in Childhood: A Current Perspective, Optometry and Vision Science, vol. 86, No. 5, pp. 420-428, 2009. 17 Pages.
Bababekova, et al., Font Size and Viewing Distance of Handheld Smart Phones, Optometry and Vision Science, vol. 88, No. 7, pp. 795-797, 2011. 3 Pages.
Rosenfield, Computer Vision Syndrome: A Review of Ocular Causes and Potential Treatments, Opthalmic & Physiological Optics, vol. 31, pp. 502-515, 2011. 14 Pages.
Scheiman, et al., Non-Surgical Interventions for Convergence Insufficiency, Cochrane Database System Rev., 3, CD006768, 2011.
Alvarez, et al., Concurrent Vision Dysfunctions in Convergence Insufficiency with Traumatic Brain Injury, Optometry and Vision Science, vol. 89, No. 12, 2012. 23 Pages.
Goodrich, et al., Mechanisms of TBI and Visual Consequences in Military and Veteran Populations, Optometry and Visual Science, vol. 90, No. 2, pp. 105-112, 2013. 8 Pages.
Deveau, et al., Improved Vision and On-Field Performance in Baseball Through Perceptual Learning, Current Biology, vol. 24, Issue 4, Feb. 2014, pp. R146-R147 and Supplemental Information, 10 pages.
Kim, et al. Adaptive Interpupillary Distance Adjustment for Stereoscopic 3D Visualization, Proceedings of the 14$^{th}$ Annual ACM SIGCHI_NZ Conference on Computer-Human Interaction, ACM, 2015, 4 pages.
Renner, et al., The Influence of the Stereo Base on Blind and Sighted Reaches in a Virtual Environment, ACM Transactions on Applied Perception, vol. 12, No. 2, Article 7, Publication date: Mar. 2015, 18 pages.
European Search Report from EP Application No. 16828640.9 dated Dec. 17, 2018.

* cited by examiner

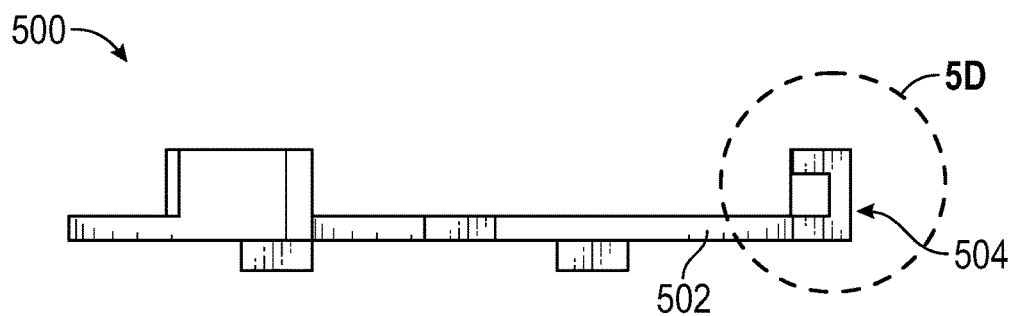
FIG. 5C
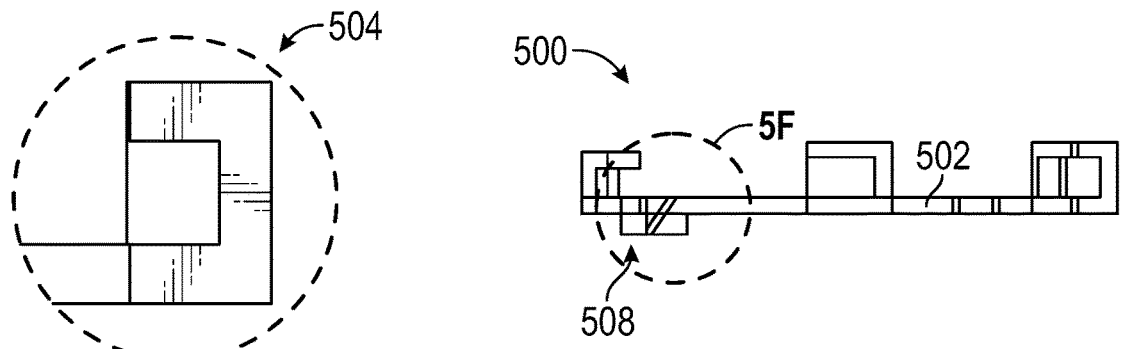
FIG. 5D
FIG. 5E
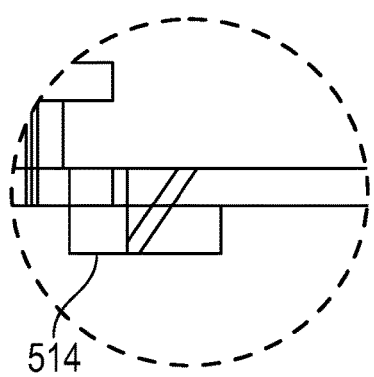
FIG. 5F

METHOD, SYSTEM, AND APPARATUS FOR TREATMENT OF BINOCULAR DYSFUNCTIONS

CROSS REFERENCE TO RELATED APPLICATIONS

This application claims the benefit of priority to U.S. Provisional Application No. 62/195,864, filed on Jul. 23, 2015, the disclosure of which is incorporated by its reference herein in its entirety.

GOVERNMENT SUPPORT

This invention was made with government support under grant CBET1228254 awarded by the National Science Foundation. The government has certain rights in the invention.

BACKGROUND

Binocular dysfunctions are present in between 4% to 8% of the general population and between 40% and 50% of the brain injury population. Some examples of binocular dysfunctions include, but are not limited to nystagmus, strabismus, convergence insufficiency (CI), convergence excess, divergence insufficiency and divergence excess. The visual symptoms of binocular dysfunctions can be exacerbated by, for example, extensive use of hand held electronic devices (e.g., smart phones, tablets, etc.) as well as by any near visual tasks (e.g., reading, computer work, etc.)—adversely impacting occupational and recreational activities of those suffering from binocular dysfunctions. When engaged in reading or other near work, asthenopic symptoms associated with binocular dysfunctions can include, but are not limited to double/blurred vision, eyestrain, visual fatigue, and headaches, which all negatively impact activities of daily living. Vision therapy is one therapeutic intervention that is commonly used to treat binocular dysfunctions.

CI is a binocular vision disorder, characterized by a reduced near point of convergence and a tendency for the eyes to drift outward (exophoria) at near compared to far visual space. Symptoms experienced by a person having CI can include blurry or double vision, headaches, eye strain, and/or difficulty sustaining attention when the person is engaged in reading and other near work. Convergence is the inward rotation of the eyes to aim the eyes at an object or objects that are located near to the person and is needed to sustain vision when looking at objects located near to the person, such as when a person is reading or working on a computer. People that have CI can experience visual symptoms within a few minutes of performing a near visual task. This is especially true for people with brain injuries that have binocular dysfunction(s).

While many forms of rehabilitation utilize repetitive patterns to improve function of a patient's eyes, such repetitive patterns can result in patient boredom, and even a lack of compliance. Protocols designed to stimulate and draw a person's attention are generally lacking in the field of vision therapy. Furthermore, in an effort to conserve resources, insurance companies typically do not pay for vision therapy or do not cover as many sessions as what would be truly needed to remediate vision symptoms. As a result, people that do not have the personal resources to pay for binocular dysfunction therapy may not receive the therapy they need and may unnecessarily suffer from the symptoms of binocular dysfunctions. Thus, there remains a need for providing techniques that can augment traditional vision therapy.

SUMMARY

Exemplary embodiments of the present disclosure relate to systems, methods, and apparatus for vision therapy. A three-dimensional (3D) game using a stereoscopic effect of a head mounted display can be controlled by eye movement. Visual stimuli incorporated in the game can be rendered to optimize vergence eye movements. For example, visual stimuli in the game can be rendered as step, ramp, combinational step and ramp, or open loop stimuli. A step is an abrupt change in vergence angular demand so the eyes moving from far to near very quickly. This is clinically referred to as a jump duction. For example, if a person held two pencils along his/her midline (one hand close to the nose and the other hand fully extended on midline) it would be the eye movement created when a person looked from the pencil in one hand and then the other. A ramp is a smooth tracking target such as a baseball batter tracking a fast ball that is approaching along visual midline. Open loop stimuli takes the current eye position and changes the current visual stimulus so as to clamp the amount of retinal disparity shown to the patient. This can be important because stimulation to just the preprogrammed component of disparity vergence is possible which can be dysfunction in patients with binocular dysfunction.

Visual stimuli can also be presented asymmetrical to the left and right eye in the 3D game to improve binocular coordination between the left and right eye. For example, one eye may have a slower inward or outward rotation compared to the eye other position when stimuli are presented along midline. Exemplary embodiments of the present disclosure can quantify the velocity of each eye, determine which eye is slower, and then adjust the visual stimulation in the game to improve symmetrical binocular coordination of the two eyes. The slower eye could be improved by increasing the velocity of the visual stimulus presented to that eye.

Some patients also have sensory dominance where one eye perceives a visual stimulus better with one eye compared to the other eye. This visual sensation is common when patients experience suppression. If patients are expressing visual suppression, exemplary embodiments of the present disclosure can adjust the visual stimuli rendered in the 3D so that the non-dominant eye sees a stronger visual stimulus compared to the dominant eye.

The visual stimuli implemented via exemplary embodiments of the present disclosure can use a Gabor Patch and/or small targets such as a small letter to reduce accommodative cues. The Gabor Patch is composed of multiple difference of Gaussian stimuli known to reduce accommodative cues. Embodiments of the 3D game can primarily evoke disparity vergence while keeping accommodative cues minimal and can be used for therapeutic intervention in users with binocular vision dysfunctions. Embodiments of the 3D game can integrate eye movement position and dynamically modify the visual stimulus rendered in the 3D game based upon the user's current eye position. Embodiments of the 3D game also can integrate auditory biofeedback to output sounds that can help a user learn to control his/her eye movements. Embodiments of the 3D game can potentially engage a user's attention more compared to conventional clinical therapeutic interventions.

In accordance with embodiments of the present disclosure, a method for remediating visual symptoms in a user with binocular dysfunction is disclosed. The method includes rendering a visual therapy video game on one or more displays, and controlling accommodative and proximal vergence stimulation of a user's eyes via the visual therapy video game. The visual therapy video game can be rendered by a head mounted display with integrated eye tracking hardware and software. A preprogrammed portion of disparity vergence can be stimulated by the visual therapy video game and a feedback portion of disparity vergence can be limited. The visual therapy video game can be a virtual reality video game and/or can include one or more visual cues to limit accommodative stimulation.

In accordance with embodiments of the present disclosure, a left eye or a right eye of the user can be asymmetrically stimulated via the visual therapy video game based on peak velocity differences between the left and right eyes. A magnitude of asymmetrical stimulation can be derived from a position of the left and right eyes. The magnitude of asymmetrical stimulation can dynamically change to limit visual suppression.

In accordance with embodiments of the present disclosure, real-time physical eye movements of the left and right eyes of the user can be detected and can be used as inputs for the visual therapy video game. A point in a three-dimensional virtual reality space to which the user's left and right eyes are fused can be determined based on the real-time physical eye movements.

In accordance with embodiments of the present disclosure, a method for treating binocular dysfunction is disclosed. The method includes fitting a user with a head mounted display configured to render a virtual reality video game and to limit accommodative stimulation and proximal vergence stimulation, stimulating disparity vergence via the virtual reality video game to stimulate a preprogrammed portion of disparity vergence and limit a feedback portion of disparity vergence, and asymmetrically stimulating a left eye or a right eye of the user via visual stimuli displayed by the virtual reality video game rendered by the head mounted display. The left eye and the right eye are asymmetrically stimulated based on an asymmetrical peak velocity difference between the left and right eyes. The method further includes asymmetrically stimulating the left eye or the right eye of the user via the virtual reality video game rendered by the head mounted display to limit visual suppression. The virtual reality video game can be render stereoscopically to render the virtual reality video game in three-dimensional virtual space.

The head mounted display can include a left eye (or first) display a right eye (or second) display configured to render the virtual reality video game and can include a right eye image capturing device disposed proximate to the right eye display and a left eye image capturing device disposed proximate to the left eye image capturing device, and the method can further include determining the asymmetrical peak velocity difference between the left and right eyes based in images of the left and right eyes captured by the left and right image capturing devices and the left and right eyes move in response to viewing the left and right eye displays. A focal length between the right eye and the right eye display when the head mounted display is fitted to the user's head. The method can also include dynamically adjusting a magnitude of the asymmetrical stimulation in the virtual reality video game to limit visual suppression.

In accordance with embodiments of the present disclosure, a system for remediating visual symptoms in a user with binocular dysfunction is disclosed. The system includes a computing system and a head mounted display. The computing system is configured to execute a visual therapy video game. The head mounted display is operatively coupled to the computing system. The head mounted display includes a left eye display; a right eye display; one or more display controllers configured to render images on the left eye display and the right eye display of the head mounted display to generate a stereoscopic effect; a first image capturing device disposed proximate to the left eye display; and a second image capturing device disposed proximate to the right eye display. The first image capturing device is configured to capture images of a left eye of a user of the head mounted display and the second image capturing device is configured to capture images of a right eye of the user. The computing system outputs the visual therapy video game to the head mounted display. The head mounted display outputs positions of the right and left eyes based on the images captured by the first and second image capturing devices and the computing system controls the visual therapy video game based on the positions of the right and left eyes. Advancement in the visual therapy video game is controlled based on a detection that the left and right eyes of the user fuses on visual stimuli in the visual therapy video game. The left and right eye displays can render the visual therapy video game to stimulate a preprogrammed portion of disparity vergence and limit a feedback portion of disparity vergence. In response to execution of the visual therapy video game by the computing system, the left eye display or the right eye display can render the visual therapy video game to asymmetrically stimulate the left eye or the right eye of the user. The asymmetrical stimulation can be based on peak velocity differences between the left and right eyes. A magnitude of asymmetrical stimulation is derived from a position of the left and right eyes.

Any combination and/or permutation of embodiments is envisioned. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

So that those having ordinary skill in the art will have a better understanding of how to make and use the disclosed systems and methods, reference is made to the accompanying figures wherein:

FIGS. 5A-F depict another exemplary mechanical fixture that can be utilized to support eye tracking components in embodiments of the head mounted display.

DETAILED DESCRIPTION

Figure 1:
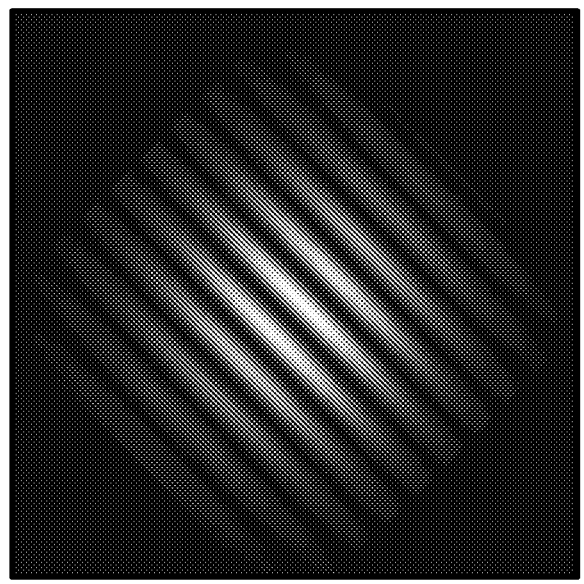
FIG. 1 shows an example of the Gabor patch.

Exemplary embodiments of the present disclosure stimulate and engage a person having a binocular dysfunction to facilitate repetitive eye motions that involve convergence (inward rotation of the eyes) and/or divergence (outward rotation of the eyes) in different positions of gaze under controlled conditions while suppressing accommodative vergence visual cues. To achieve this, exemplary embodiments can utilize three-dimensional (3D) vision in a game environment. Unique features of this environment can advantageously include objective monitoring of the accuracy of eye alignment, and correlating progress in the game to accurate eye movements. Such features are typically not available as a part of conventional vision therapy procedures. For example, using conventional vision therapy procedures, a therapist or a parent/caregiver works with a patient to determine whether the procedure is being performed correctly. By incorporating objective eye movement monitoring into exemplary embodiments of the present disclosure, exemplary embodiments of the present disclosure can determine whether a patient is performing a convergence and/or divergence technique properly, and can control the patient's progress through a game based on a determination that the patient is or is not performing the technique(s) properly. Auditory feedback can be used to alert a patient when he/she is or is not properly maintaining a position of one or both eyes.

Exemplary embodiments of the present disclosure can utilize a head mounted display to generate the 3D vision (e.g., using the stereoscopic effect), where each eye receives an image of the same object or scene at slightly different angles or points-of-view. The head mounted display provides a constant focal length from the patient's eye, and thereby reduces accommodative stimulation. Use of visual stimuli (e.g., such as Gabor patches which use difference of Gaussian or small letters) in the images displayed to the user via the head mounted display can further reduce accommodative stimulation.

In exemplary embodiments of the present disclosure, the head mounted display advantageously provides a virtual reality gaming environment that can form a platform for therapeutic intervention that has the potential to significantly improve the activities of daily living of people that have a binocular dysfunction via, for example, improved user compliance and effort during vision therapy. Thus, a virtual reality game can be designed that use embodiments of the head mounted displays described herein and incorporate clinical techniques in a fun, creative and stimulating manner while still providing therapeutically effective treatment of binocular dysfunctions.

Using embodiments of the head mounted display described herein, exemplary embodiments of the present disclosure can implement a virtual reality game that uses eye positions of the user to adjust visual stimulus being presented to the user; thereby concentrating the visual rehabilitation to optimize a preprogrammed portion of disparity vergence and to reduce the influence of a feedback controlled portion of disparity vergence.

Vision therapy has many different procedures or forms where one commonality between many of the techniques is to keep the blur stimulus to the accommodation system constant while varying the stimulation to the disparity vergence system. Disparity is the difference between the current target projected to the retina and where a new target of interest falls on the retina. The current gaze or visual fixation point has the current target of interest project to the fovea. The fovea is the portion of the retina which has the highest density of photoreceptors or the 'high definition' portion of the retina. The reason we move our eyes is to project objects of interest to the fovea. If the new intended target is projected more nasally (along midline) to the back of the retina then the eyes must rotate outward or perform a divergence movement. Conversely, if the new intended target is projected more laterally (towards the ears) to the back of the retina then the eyes must rotate inward or perform a convergence movement.

As described herein, people with convergence insufficiency can have visual symptoms when engaged in near work (i.e. reading). To strengthen the disparity convergence system, stimuli that evoke inward or outward rotation of the eyes should be provided that generally do not stimulate accommodation or blur. Exemplary embodiments of the present disclosure can be advantageously configured to display right and left images via the head mounted display that include objects intended to stimulate eye movement without stimulating accommodation or blur. As such, the 3D gaming environment for vision therapy in accordance with exemplary embodiments of the present disclosure can stimulate disparity vergence while keeping accommodation and accommodative vergence constant. As one non-limiting example, a game can be designed that renders images via the head mounted display that include objects on which a user typically cannot focus clearly. For example the game can be rendered by to include objects at which the user aims his/her eyes (e.g., based on convergence or divergence) that are formed using the Gabor patch. The Gabor patch uses a series of differences of Gaussians (DOG) stimuli which appear as blurry lines, such as those shown in the exemplary Gabor patch 100 of FIG. 1. The visual system cannot focus on objects that are formed with the Gabor patch; hence the accommodative system is minimally stimulated by exemplary embodiments of the present disclosure, which can be important for successful vision therapy. Another non-limiting example of objects that can be rendered by exemplary embodiments of the present disclosure can include small letters, which a person cannot focus on clearly.

Figure 2:
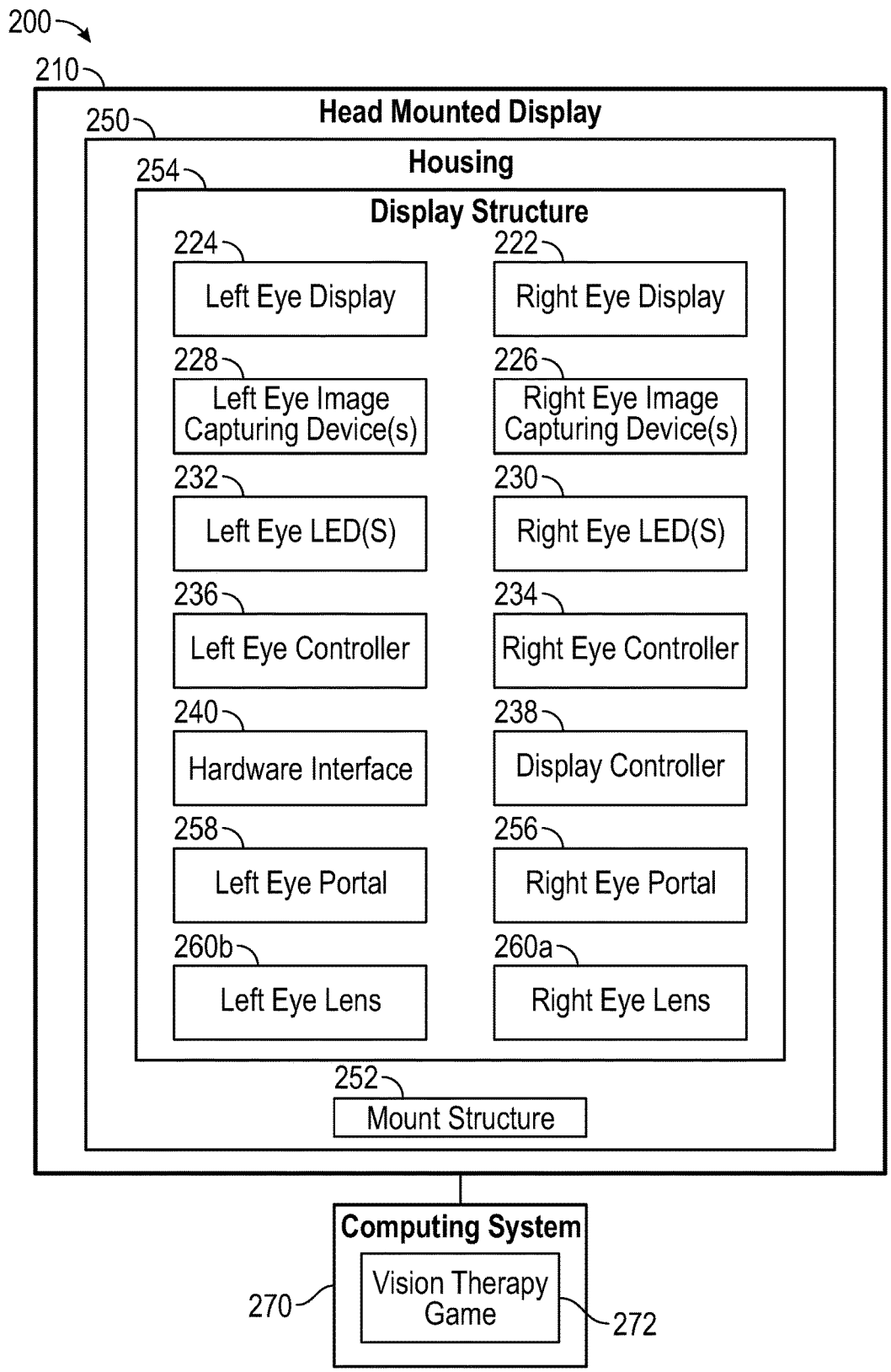
FIG. 2 shows an exemplary vision therapy system in accordance with exemplary embodiments of the present disclosure.

FIG. 2 shows an exemplary vision therapy system 200 in accordance with exemplary embodiments of the present disclosure. The vision therapy system 200 can include a head mounted display 210 and a computing system 270. The head mounted display 210 and the computing system 270 can be communicatively coupled to each other via wireless or wired communications such that the head mounted display 210 and the computing system 270 can interact with each other to implement a gaming environment for vision therapy. For example, embodiments of the vision therapy system 200 can be configured to provide a gaming environment to treat binocular dysfunctions, such as, but not limited to nystagmus, strabismus, convergence insufficiency (CI), convergence excess, divergence insufficiency and divergence excess.

The head mounted display 210 include circuitry disposed within a housing 250. The circuitry can include a right eye display 222, a left eye display 224, one or more right eye image capturing devices 226, one or more left eye image capturing devices 228, one or more right eye light emitting diodes 230, one or more left eye light emitting diodes 232, a right eye controller 234, a left eye controller 236, one or more display controllers 238, and one or more hardware interfaces 240. While any head mounted display including the aforementioned components can be utilized to implement embodiments of the present disclosure, an example embodiment can utilized a modified Oculus Rift DK2 headset.

The right and left eye displays 222 and 224 can be disposed within the housing 250 such that the right display is positioned in front of the right eye of the user when the housing 250 is mounted on the user's head and the left eye display 224 is positioned in front of the left eye of the user when the housing 250 is mounted on the user's head. In this configuration, the right eye display 222 and the right eye display 224 can be controlled by the one or more display controllers 238 to render images on the right and left eye displays 222 and 224 to induce a stereoscopic effect, which can be used to generate three-dimensional images, where objects in the images can be perceived by the user's vision system as being at different depths while maintaining constant focal length between the user's right eye and the right eye display 222 and between the user's left eye and the left eye display 224. In exemplary embodiments, the right eye display 222 and/or the left eye display 224 can be implemented as a light emitting diode display, an organic light emitting diode (OLED) display (e.g., passive-matrix (PMOLED) display, active-matrix (AMOLED) display), and/or any suitable display.

The one or more right eye image capturing devices 226 can be disposed in the housing 250 relative to the right eye display 222 so that the one or more right eye image capturing devices 226 can be positioned and oriented to capture images of the user's right eye as the user views the right eye display 222. Likewise, the one or more left eye image capturing devices 228 can be disposed in the housing 250 relative to the left eye display 224 so that the one or more left eye image capturing devices 228 can be positioned and oriented to capture images of the user's left eye as the user views the left eye display 224. In exemplary embodiments, the one or more right and left eye image capturing devices 222 and 224 can be infrared (IR) cameras configured to have a particular sensitive to IR light (e.g., to capture images of IR radiation).

The one or more right eye light emitting diodes 230 can be disposed in the housing 250 relative to the right eye display 222 and the one or more right eye light emitting diodes so that the one or more light emitting diodes 230 can be positioned and oriented to emit light towards the user's right eye as the user views the right eye display 222. Likewise, the one or more left eye light emitting diodes 232 can be disposed in the housing 250 relative to the left eye display 224 so that the one or more left eye light emitting diodes 232 can be positioned and oriented to emit light towards the user's left eye as the user views the left eye display 224. In exemplary embodiments, the one or more right and left eye light emitting diodes 230 and 232 can be infrared (IR) light emitting diodes configured to emit IR light. In some embodiments, the light emitting diodes project infrared light into the eye at about ten percent (10%) of the safety limit.

The right eye controller 234 can be operatively coupled to the one or more right eye image capturing devices 226 to control an operation of the one or more right eye image capturing devices 226 and/or to process the images of the right eye captured by the one or more right eye image capturing devices 226. Likewise, the left eye controller 236 can be operatively coupled to the one or more left eye image capturing devices 228 to control an operation of the one or more left eye image capturing devices 228 and/or to process the images of the left eye captured by the one or more left eye image capturing devices 228. As one non-limiting example, the right and left eye controllers 234 and 236 can be configured to control a shutter, aperture, refresh rate, discharge rate, and the like of the one or more right and left eye image capturing devices 222 and 224, respectively. As another non-limiting example, the right and left eye controllers 234 and 236 can monitor and/or track the movement of the user's right and right eyes as the user views the right and left eye displays 226, respectively, which can be utilized by exemplary embodiments to effect vision therapy of the user for binocular dysfunctions. While separate controllers in the form of the right and left eye controllers 234 and 236 are utilized to control and interface with the right and left eye image capturing device 222 and 224, exemplary embodiments of the present disclosure can be implemented with a single integrated controller to control and interface with the right and left eye image capturing devices 222 and 224.

In some embodiments, the right eye controller 234 and/or left eye controller 236 can be implemented with Raspberry Pi microcomputers configured to detect eye motion using a proprietary eye-tracking software. The eye-tracking software can be developed in C++ and OpenCV, a real-time video processing library, and/or can be developed utilizing any suitable programming and/or scripting languages. In some embodiments, the eye tracking system (e.g., including the image capturing devices and the right and left eye controls) is capable of real-time eye tracking of about 40 frames per second. The light emitting diodes (e.g., operating as IR light sources) illuminate each eye in a dark environment of the head mounted display. A grayscale image is thresholded to a binary image. A value of gray can be chosen which provides the best contrast between a pupil and a remainder of the eye. A window aperture can be utilized to isolate the eye to improve detection of the pupil within the eye. Darker shades than the threshold can be kept (black) and lighter shades than the threshold can be removed (white). Then, a green cross can be overlaid on the centroid of the original image. The pupil, the hole in the eye through which light is absorbed, does not reflect light, and is thus the darkest spot on the binary image, which can facilitate tracking of the center of the pupil. The centroid tracking information can be sent to computing system via a User Datagram Protocol (UDP), which is an internet protocol suite for fast data transmission, for processing.

The one or more display controllers 238 can be operatively coupled to right and left eye displays 222 and 224 to control an operation of the right and left eye displays 222 and 224 in response to input received from the computing system 270 and in response to positions of the user's right and left eyes as described herein. In exemplary embodiments, the one or more display controllers 238 can be configured to render images on the right and left eye displays of the same scene and/or objects, where images of the scene and/or objects are render at slightly different angles and/or points-of-view to facilitate the stereoscopic effect. In exemplary embodiments, the one or more display controllers 238 can include graphical processing units.

The one or more hardware interfaces 240 can facilitate communication between the head mounted display 210 and the computing system 270. The head mounted display 210 can be configured to transmit data to the computing system 270 and to receive data from the computing system 270 via the one or more hardware interfaces 240. As one example, the one or more hardware interfaces 240 can be configured to receive data from the computing system 270 corresponding to images and can be configured to transmit the data to the one or more display controllers 238, which can render the images on the right and left eye displays 222 and 224 to provide a game in three-dimensions (e.g., as a result of the stereoscopic effect) that is designed to facilitate vision therapy for binocular dysfunctions. Likewise, the one or more hardware interfaces 240 can receive data from the right and left eye controllers 234 and 236 corresponding to right and left eye positions or angles of the user, respectively, and can transmit the data to the computing system 270, which can use the data to control an operation of the game to facilitate vision therapy for binocular dysfunctions (e.g., by confirming that the user is properly converging and diverging on specific objects in the game).

The housing 250 can include a mounting structure 252 and a display structure 254. The mounting structure 252 allows a user to wear the head mounted display 210 on his/her head and to position the display structure over his/her eyes to facilitate viewing of the right and left eye displays 222 and 224 by the right and left eyes of the user, respectively. The mounting structure can be configured to generally mount the head mounted display 210 on a user's head in a secure and stable manner. As such, the head mounted display 210 generally remains fixed with respect to the user's head such that when the user moves his/her head left, right, up, and down, the head mounted display 210 generally moves with the user's head.

The display structure 254 can be contoured to fit snug against a user's face to cover the user's eyes and to generally prevent light from the environment surrounding the user from reaching the user's eyes. The display structure 254 can include a right eye portal 256 and a left eye portal 258 formed therein. A right eye lens 260a can be disposed over the right eye portal and a left eye lens 260b can be disposed over the left eye portal. The right eye display 222, the one or more right eye image capturing devices 226, and the one or more right eye light emitting diodes 230 can be disposed within the display structure 254 behind the lens 260 covering the right eye portal 256 such that the lens 256 is disposed between the user's right eye and each of the right eye display 222, the one or more right eye image capturing devices 226, and the one or more right eye light emitting diodes 230. The left eye display 224, the one or more left eye image capturing devices 228, and the one or more left eye light emitting diodes 232 can be disposed within the display structure 254 behind the lens 260 covering the left eye portal 258 such that the lens 260 is disposed between the user's left eye and each of the left eye display 224, the one or more left eye image capturing devices 228, and the one or more left eye light emitting diodes 232.

While the one or more right eye image capturing devices 226 and the one or more right eye light emitting diodes 230 are described as being disposed behind the lens 260 covering the right eye portal as an example embodiment, in exemplary embodiments of the present disclosure the one or more right eye image capturing devices 226 and/or the one or more right eye light emitting diodes 230 can be disposed in front of and/or around the lens 260 covering the right eye portal such that lens 260 is not positioned between the user's right eye and the one or more right eye image capturing devices 226 and/or the one or more right eye light emitting diodes 230. Likewise, while the one or more left eye image capturing devices 228 and the one or more left eye light emitting diodes 232 are described as being disposed behind the lens 260 covering the left eye portal as an example embodiment, in exemplary embodiments of the present disclosure the one or more left eye image capturing devices 228 and/or the one or more left eye light emitting diodes 232 can be disposed in front of and/or around the lens 260 covering the left eye portal such that lens 260 is not positioned between the user's left eye and the one or more right eye image capturing devices 226 and/or the one or more right eye light emitting diodes 230.

The computing system 270 can be configured to execute one or more application and/or programs to execute a visual therapy game 272 designed to administer vision therapy for binocular dysfunctions via the head mounted display 210. The game can include images that includes objects at which the user's eyes are naturally drawn or at which the user is instructed to aim his/her eyes. The objects can be formed using one or more techniques to reduce stimulation of accommodation and/or blur. For example, the objects can be formed using the Gabor patch, small letters, and/or any other techniques that reduce stimulation of accommodation and/or blur. The game can be configured to react dynamically to the position and/or angle of the user's eyes as the user attempts to aim his/her eyes at the objects and/or can allow the user move the objects based on the position and/or angle of the user's eyes. In addition to tacking a users' eye to advance in the game being played, the head mounted display can track and/or monitor a position of the of the user's eyes relative to an expected and/or desired position of the user's eyes to capture vergence parameters which can be output to the computing system 270 (and transmitted from the computing system to a remote computing system) to facilitate quantitative and/or qualitative assessment by a clinician. In exemplary embodiments, the head mounted display 210 and/or the computing system 270 can limit an amount of time a user can play the games for visual therapy to a maximum time limit to provide a safety mechanism so that the user's eyes are overly exposed to infrared light emitted by the one or more light emitting diodes of the head mounted display. Non-limiting examples of various games are described herein to illustrate embodiments of the present disclosure.

To facilitate game play, the computing system 270 transmits data to the head mounted display 210 include right and left images to be rendered by the right and left eye displays 222 and 224. In response to rendering the right and left images, the user's visual system can perceive the right and left images as a single image in three-dimensional space (e.g., using the stereoscopic effect). The right and left images rendered on the right and left eye displays 222 and 224, respectively, can be offset from each other so that to fuse some objects, the visual system must converge more than other objects. The more converged the eyes, the closer a visual object will appear to the person within a head mounted display. The position and/or angle of the user's eyes can be adjusted based on the objects included in the right and left images and the one or more right and left image capturing devices 226 and 228, respectively, can track the position and/or angle of the user's eye, which can be transmitted to the computing system 270. The computing system can receive the position and/or angle of the user's eyes as inputs in response to the right and left images being displayed. For example, the position of the right and left eye of the user can be tracked to determine a point in three-dimensional virtual reality space at which the user's eyes are fused. Based on the monitored or tracked eye position and/or angle, the computing system 270, executing the game, can generate subsequent right and left images to invoke convergence or divergence in a controlled manner to administer visual therapy for binocular dysfunctions. By allowing the user to control the game play based on the position and/or angle of the user's eyes, the user's ability to properly converge or diverge his/her eyes as required by the game can ensure that the user is performing the visual therapy for binocular dysfunctions (e.g., the user's eyes converging or diverging in accordance with the visual therapy being administered via the game). In exemplary embodiments, the user may be required to reach designated levels of vergence angular demand (varying amounts of going cross-eyed/converged) before she/he can fuses at a 3D model character. More advanced settings of the game can require the user to sustain convergence for longer periods of time before a successful action can be taken.

Some examples of visual stimuli that can be incorporated into the right and left images of the game to optimize vergence eye movements can include sequences of right and left images that create animations of objects in three-dimensions, where the animations of the objects includes, for example, step, ramp, combinational step and ramp, or open loop stimuli. The visual stimuli render in the right and left images of the right and left eye displays can stimulate a preprogrammed portion of disparity vergence while minimizing the feedback portion of disparity vergence, can asymmetrically stimulate a left eye or a right eye of the user based on an asymmetrical peak velocity difference between the left and right eyes (one eye is slower compared to the other), which can be detected and/or measured by the eye tracking included in the head mounted display and/or can be determined using other techniques, and/or can asymmetrically stimulate the left eye or the right eye of the user to reduce visual suppression. The game can be controlled by the computing system 270 to control a magnitude of the visual stimuli rendered in the right and left images of the right and left eye displays of the head mounted display based on positions of the right and left eyes detected via the eye tracking of the head mounted display (e.g., via the right and left image capturing devices and right and left eye controllers of embodiments of the head mounted display). For example, a magnitude of the asymmetrical stimulation to the right or left eye can be derived from a position of the right and left eyes of the user dynamically determined by the right and left eye controllers of embodiments of the head mounted display. The magnitude of visual stimuli of the game rendered via the right and left eye displays of the head mounted display can also be dynamically changed to reduce visual suppression.

In embodiments of the games executed by the visual therapy system 100, the games can have four settings: beginner, intermediate, advanced and custom. Three settings (beginner, intermediate, and advanced) can be preprogrammed settings that can be used for a majority of users with binocular dysfunctions. The custom setting will allow for adjustment to the angular vergence demand (e.g., by a clinician), e.g., to adjust the amount of time needed for fusion and the type of visual stimuli presented during the game. Vision parameters include but are not limited to quantitative measurement of near point of convergence, positive fusion range, dissociated phoria, vergence fixation times, vergence peak velocity, vergence time constant, accuracy of eye alignment, and amount of time the vision therapy is administered. Vision parameters can be sent to the clinician automatically and stored within a spread sheet.

By fixing the focal length or the distance between the lens within the eye and the head mounted display, exemplary embodiments of the present disclosure can reduce accommodative stimulation during game play. The accommodative stimulation can be further reduced during game play using object formation techniques that reduce stimulation of accommodation and/or blur.

Another attribute of the embodiments of the present disclosure is the therapeutic visual game, which is controlled with eye position. While most games use a joystick, hand motion, body motion or another physical device to move to target objects within a game, exemplary embodiments of the games described herein use eye position to lock onto visual stimuli within the game. The user must reach designated levels of vergence angular demand (varying amounts of going cross-eyed/converged) before s/he can fuse a 3D model character. More advanced settings of the game can require the operator to sustain convergence for longer periods of time in order to fire at the 3D model character.

While an example embodiment has been illustrated including a head mounted display 210 and a computing system 270, exemplary embodiments of the present disclosure can be configured such that the head mounted display includes the computing system 270 and/or is configured to perform the functions and operations of the computing system 270 such that the head mount display 210 is a self-contained, stand-alone device that provides vision treatment for binocular dysfunctions in a gaming environment as described herein.

Figure 3:
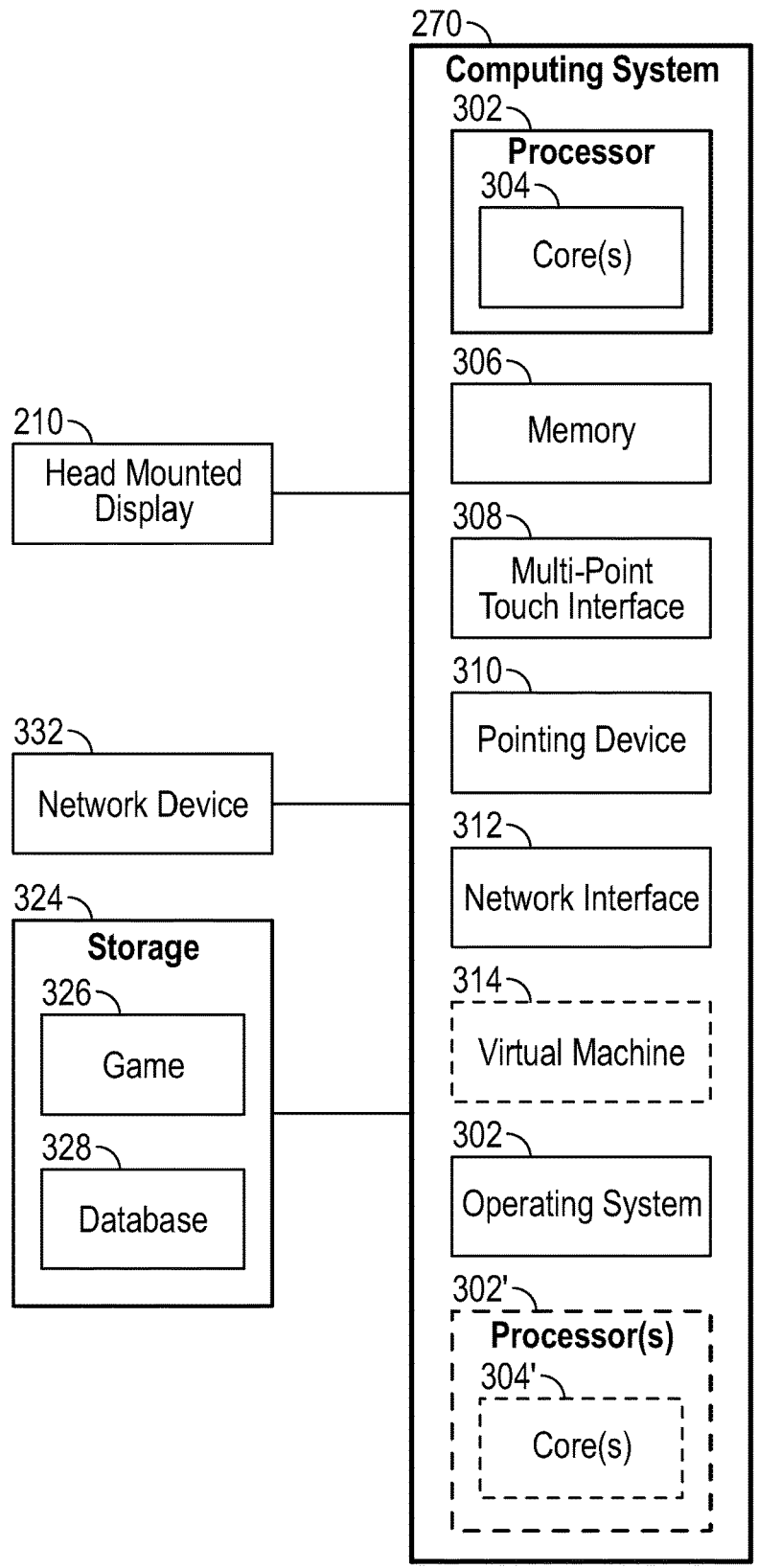
FIG. 3 is a block diagram of an exemplary embodiment of the computing system shown in FIG. 2.

FIG. 3 is a block diagram of an exemplary embodiment of the computing system 270. In some embodiments, the computing system 270 can be a gaming console configured to execute virtual reality games to be rendered through embodiments of the head mounted display 210. The computing system 270 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives), and the like. For example, memory 306 included in the computing system 270 may store computer-readable and computer-executable instructions or software for implementing exemplary embodiments. The computing system 270 also includes processor 302 and associated core 304, and optionally, one or more additional processor(s) 302' and associated core(s) 304' (for example, in the case of computer systems having multiple processors/cores), for executing computer-readable and computer-executable instructions or software stored in the memory 306 and other programs for controlling system hardware. Processor 302 and processor(s) 302' may each be a single core processor or multiple core (304 and 304') processor and may be central processing units, graphical processing units, and the like.

Virtualization may be employed in the computing system 270 so that infrastructure and resources in the computing device may be shared dynamically. A virtual machine 314 may be provided to handle a process running on multiple processors so that the process appears to be using only one computing resource rather than multiple computing resources. Multiple virtual machines may also be used with one processor.

Memory 306 may include a computer system memory or random access memory, such as DRAM, SRAM, EDO RAM, and the like. Memory 306 may include other types of memory as well, or combinations thereof.

A user may interact with the computing system 270 through an embodiment of the head mounted display 210, which can display one or more virtual reality games in accordance with exemplary embodiments. The computing system 270 may include other I/O devices for receiving input from a user, for example, a keyboard or any suitable multi-point touch interface 308, a pointing device 310 (e.g., a mouse or joystick). The computing device 270 may include other suitable conventional I/O peripherals.

The computing system 270 may also include one or more storage devices 324, such as a hard-drive, CD-ROM, or other computer readable media, for storing data and computer-readable instructions and/or software that implement exemplary embodiments of one or more virtual reality games to facilitate visual therapy for binocular dysfunctions. For example, the storage device can store a game 326. Exemplary storage device 324 may also store one or more databases for storing any suitable information required to implement exemplary embodiments. For example, exemplary storage device 324 can store one or more databases 328 for storing information, such as user performance, user milestones, a state associated with a game being executed by the computing system 300, and the like. The databases may be updated at any suitable time to add, delete, and/or update one or more items in the databases.

The computing system 270 can include a network interface 312 configured to interface via one or more network devices 322 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 312 may include a built-in network adapter, network interface card, PCMCIA network card, card bus network adapter, wireless network adapter, USB network adapter, modem or any other device suitable for interfacing the computing system 270 to any type of network capable of communication and performing the operations described herein. Moreover, the computing system 270 may be any computer system, such as a workstation, desktop computer, server, laptop, handheld computer, tablet computer (e.g., the iPad™ tablet computer), mobile computing or communication device (e.g., the iPhone™ communication device), or other form of computing or telecommunications device that is capable of communication and that has sufficient processor power and memory capacity to perform the operations described herein.

The computing system 270 may run any operating system 316, such as any of the versions of the Microsoft® Windows® operating systems, the different releases of the Unix and Linux operating systems, any version of the MacOS® for Macintosh computers, any embedded operating system, Microsoft® Xbox operating systems for Xbox gaming systems, Playstation operating systems for PlayStation gaming systems, Wii operating systems for Wii gaming systems, any real-time operating system, any open source operating system, any proprietary operating system, or any other operating system capable of running on the computing device and performing the operations described herein. In exemplary embodiments, the operating system 316 may be run in native mode or emulated mode. In an exemplary embodiment, the operating system 316 may be run on one or more cloud machine instances.

Figure 4:
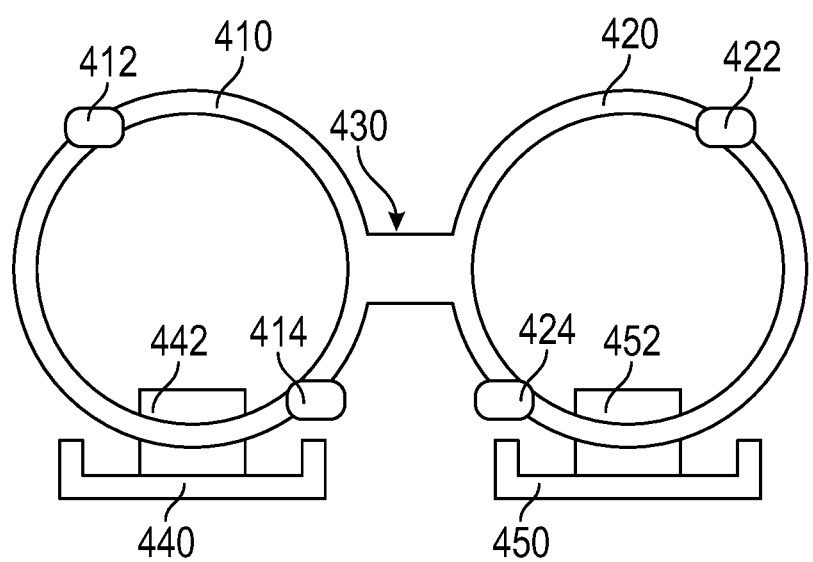
FIG. 4 depicts a schematic diagram of an exemplary mechanical fixture that can be utilized to support eye tracking components in embodiments of the head mounted display.

FIG. 4 depicts a schematic diagram of an exemplary mechanical fixture 400 that can be utilized to support eye tracking components in embodiments of the head mounted display (e.g., the head mounted display 210). The mechanical fixture 400 can support the right and left eye light emitting diodes, the right and left image capturing device(s), and the right and left eye controllers described herein. The mechanical fixture 400 can be embedded in embodiments of the head mounted display. The mechanical fixture 400 can include a rings 410 and 420, a bridging portion 430 joining the rings 410 and 420, and imaging mounts 440 and 450. The ring 410, the ring 420, and the bridging portion 430 can be dimensioned to be disposed within or on the display structure of the head mounted display. For example, the ring 410 can be configured to correspond to the left eye portal of the display structure, the ring 420 can be configured to correspond to the right eye portal of the display structure, and the bridging portion 430 can be configured to extend between the rings 410 and 420 such that the rings 410 and 420 are spaced apart from each other at a distance that corresponds to a distance by which the left and right eye portals are spaced apart. The bridging portion 430 can also be used to mount the mechanical fixture 400 with respect to the left and right eye portals of the display structure.

As shown in FIG. 4, the ring 410 can include light emitting diodes 412 and 414 that can be configured to emit light (infrared light) towards the left eye of the user when the user is wearing embodiments of the head mounted display that include the mechanical fixture 400. The light emitting diodes 412 and 414 can be diametrically opposed from each other. While an exemplary embodiment is illustrated in which the two light emitting diodes 412 and 414 are diametrically opposed, in exemplary embodiments of the present disclosure can be disposed about the ring 410 in any suitable configuration. Furthermore, while an exemplary embodiment is illustrated that includes two light emitting diodes, exemplary embodiments of the present disclosure can include a single light emitting diode or can include more than two light emitting diodes. For embodiments that include more than two light emitting diodes, the light emitting diodes can be disposed about the ring 410 in any suitable configuration.

The imaging mount 440 can be disposed towards a bottom portion of the ring 410 and can include a bracket 442 configured to retain and support the left eye controller and the one or more left eye image capturing devices of embodiments of the head mounted display. For example, the imaging mount 440 can be disposed approximately ninety degrees clockwise relative to the bridging portion 430 joining the rings 410 and 420. While an exemplary embodiment is illustrated in which the imaging mount 440 is disposed towards a bottom of the ring 410, in exemplary embodiments, the imaging mount 440 can be disposed about the ring 410 in any suitable configuration.

The ring 420 can include light emitting diodes 422 and 424 that can be configured to emit light (infrared light) towards the right eye of the user when the user is wearing embodiments of the head mounted display that include the mechanical fixture 400. The light emitting diodes 422 and 424 can be diametrically opposed from each other. While an exemplary embodiment is illustrated in which the two light emitting diodes 422 and 424 are diametrically opposed, in exemplary embodiments of the present disclosure can be disposed about the ring 420 in any suitable configuration. Furthermore, while an exemplary embodiment is illustrated that includes two light emitting diodes, exemplary embodiments of the present disclosure can include a single light emitting diode or can include more than two light emitting diodes. For embodiments that include more than two light emitting diodes, the light emitting diodes can be disposed about the ring 420 in any suitable configuration.

The imaging mount 450 can be disposed towards a bottom portion of the ring 420 and can include a bracket 452 configured to retain and support the right eye controller and the one or more one eye image capturing devices of embodiments of the head mounted display. For example, the imaging mount 450 can be disposed approximately ninety degrees counter-clockwise relative to the bridging portion 430 joining the rings 410 and 420. While an exemplary embodiment is illustrated in which the imaging mount 450 is disposed towards a bottom of the ring 420, in exemplary embodiments, the imaging mount 450 can be disposed about the ring 420 in any suitable configuration.

Figure 5A:
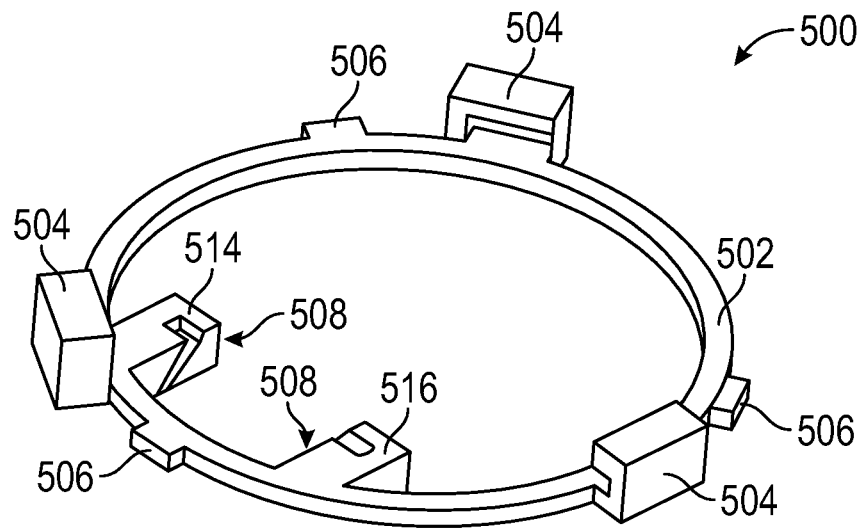
Figure 5B:
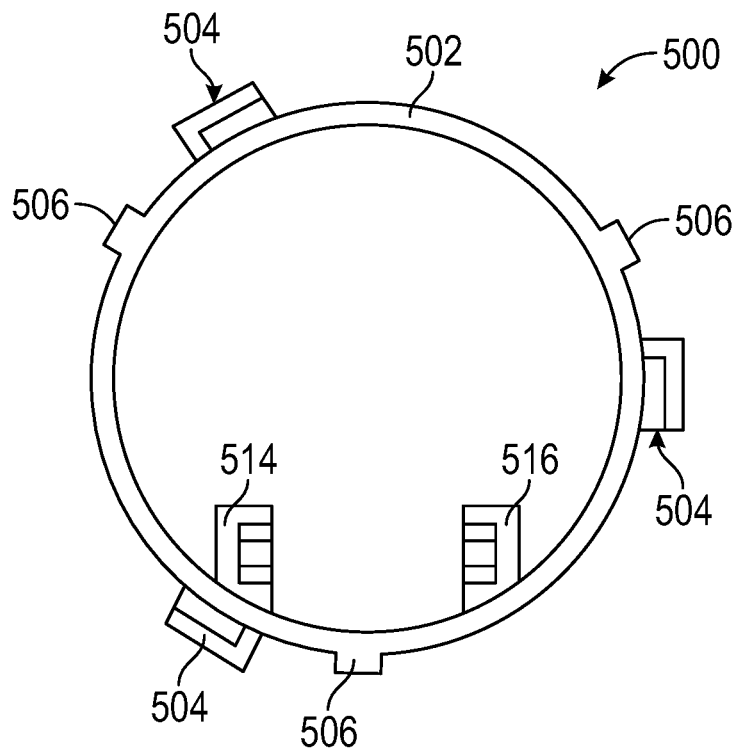
Figure 6:
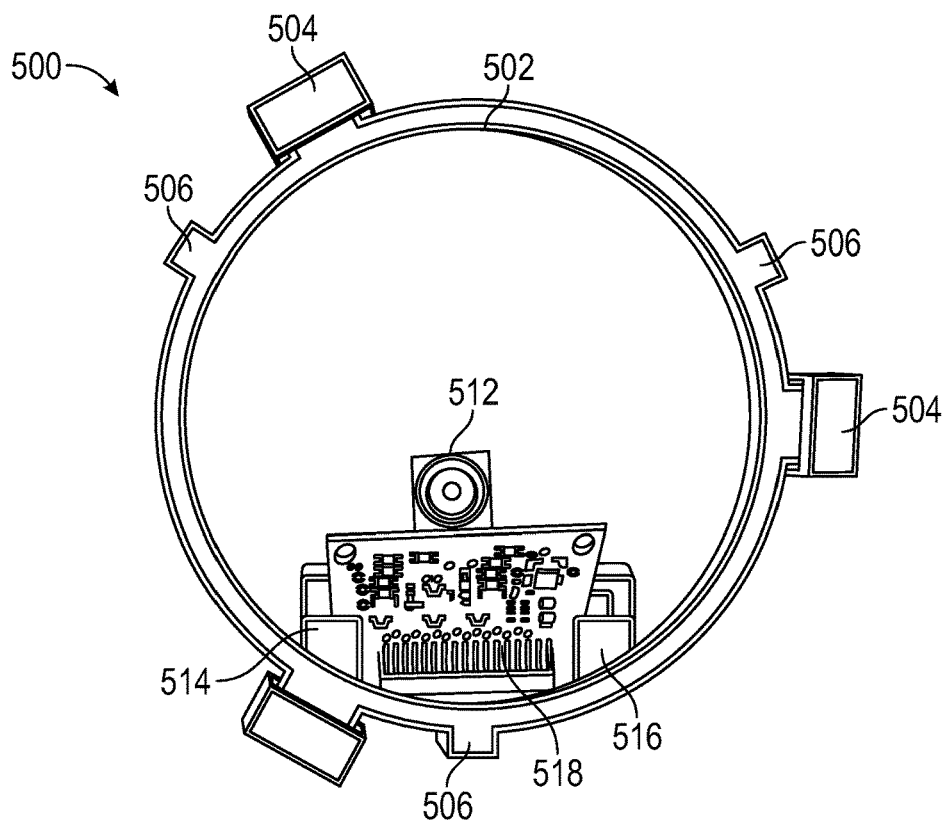
FIG. 6 depicts an embodiment of the mechanical fixture shown in FIGS. 5A-F with a controller and image capturing device mounted thereto.

FIGS. 5A-F and 6 depicts an exemplary mechanical fixture 500 that can be utilized to support eye tracking components in embodiments of the head mounted display. FIG. 5A provides a perspective view of the mechanical fixture 500. FIG. 5B provides a plan view of the mechanical fixture 500. FIG. 5C provides a side view of the mechanical fixture 500. FIG. 5D provides a section view of a portion of the mechanical fixture 500 from FIG. 5C. FIG. 5E provides a cross section of the mechanical fixture 500. FIG. 5F provides a section view of a portion of the mechanical fixture 500 shown in FIG. 5E. The mechanical fixture 500 can support the right/left eye light emitting diodes, the right/left image capturing device(s), and the right/left eye controllers. The mechanical fixture 500 can be embedded in embodiments of the head mounted display.

As shown in FIGS. 5A-F, the mechanical fixture 500 can have a generally ring-shaped body 502. The body 502 can be dimensioned to correspond to the dimensions of the right/left eye portal (e.g., the body 502 can have a diameter that generally corresponds to a diameter of the right/left eye portal. Mounting members 504, alignment members 506, and an imaging mount 508 disposed about the body 502. The mounting members 504 can include one or more structures for securing, mating, or otherwise coupling the mechanical fixture 500 to the display structure of the head mounted display. For example, the mounting members 504 can include slotted axial protrusions extending from the ring-shaped body 502 for engaging portions of the display structure of the head mounted display. The alignment members 506 can be formed by radial protrusions disposed about a circumference of the ring-shaped body 502 and extending radially outward from the ring-shaped body 502. The alignment members 506 can be configured to engage portions of the display structure to ensure that the mechanical fixture is properly mounted with respect to the right/left eye portal of the display structure of the head mounted display.

Referring to FIGS. 5A-F and 6, the imaging mount 508 can be configured to support a right/left eye controller and an image capturing device 512. For example, the imaging mount 508 can include two opposingly spaced slotted radial protrusions 514 and 516 extending from the ring-shaped body 502. The protrusions 514 and 516 can extend radially inward from the ring-shaped body 502 and can be configured to receive a circuit board 518 upon which the right/left eye controller is mounted. The slots of the protrusions 514 and 516 can be configured to receive the circuit board 518 such that when embodiments of the head mounted display is worn by a user the image capturing device 512 is positioned and oriented to capture images of the user's eye without obscuring the user's vision of the right/left display.

Figure 7:
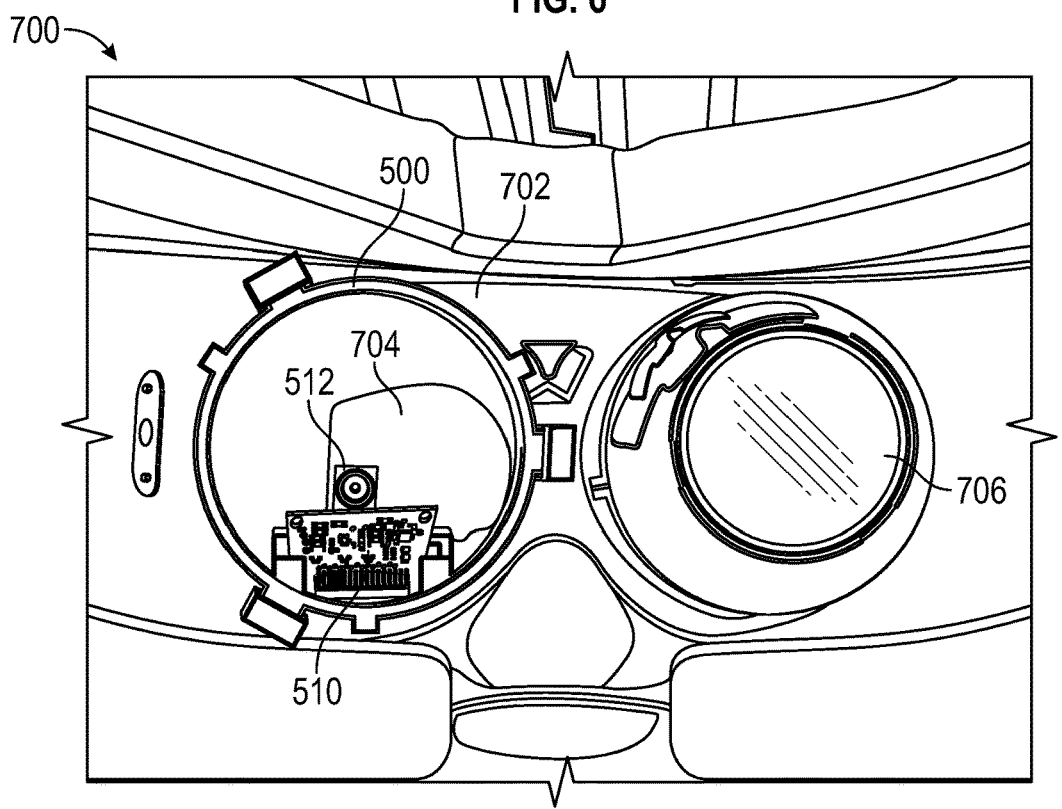
FIG. 7 shows the mechanical fixture, controller, and image capturing device in FIG. 6 mounted with respect to a left eye portal of a display structure of a head mounted display in accordance with embodiments of the present disclosure.
Figure 8:
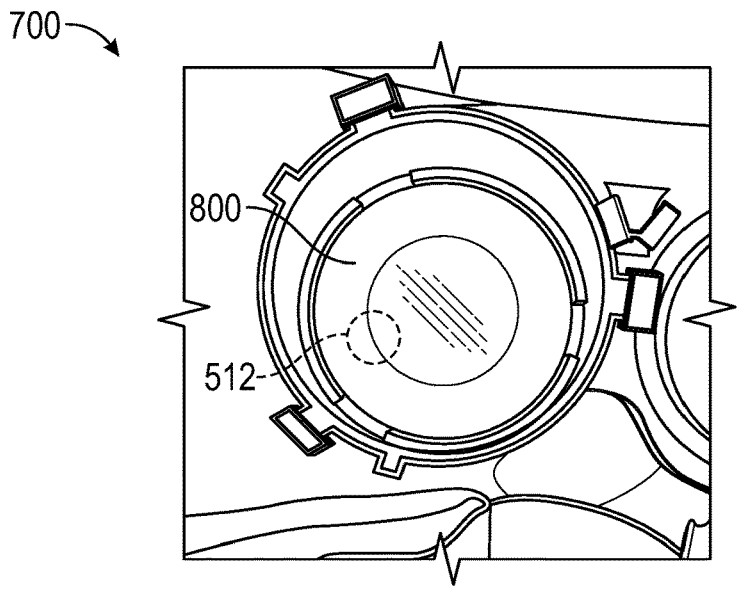
FIG. 8 depicts a portion of a head mounted display with a lens covering a mechanical fixture having eye tracking components mount thereto in accordance with embodiments of the present disclosure.

FIG. 7 depicts a portion of the display structure 700 of a head mounted display with a left lens removed to reveal a left eye portal 702, a left eye display 704, an embodiment of the mechanical fixture 500 shown in FIGS. 5A-F and 6 with the left eye controller 510 and the image capturing device 512. The right eye side of the display structure includes lens 706 mounted over the left eye portal. FIG. 8 shows a portion of the display structure with a lens 800 covering the left eye portal such that the left eye portal 702, the left eye display 704, the left eye controller 510, and the image capturing device 512 shown in FIG. 7 are disposed behind the lens 800. The image capturing device 512 can be seen through the lens 800 and a portion of the mechanical fixture 500 can be seen protruding from behind the lens 800.

While office based therapy is typically significantly more effective compared to home based vision therapies, it is unknown whether this is a result of home training techniques per se or is the result of reduced user compliance in the home setting compared to having a therapist within an office setting. As described herein many forms of rehabilitation utilize a repetitive pattern that improves function. However such repetitive patterns can easily result in user boredom. It has been recognized that poor user compliance with home-based vision therapy is a problem in the field of vision therapy because current therapy procedures lack the sophistication, graphics, quality, and excitement of currently available videogames. The use of virtual reality gaming as a platform for therapeutic intervention has the potential to significantly reduce visual symptoms via improved user compliance. The software portion of the system uses object-oriented architecture which utilizes a variety of visual parameters in a flexible architecture that will allow for a modular, object-oriented design, with the potential for the creation of a variety of games. Flexibility and modularity of code allows for future development so that the platform can be adapted for different age groups and users with various vision dysfunctions such as convergence insufficiency, strabismus, and nystagmus.

One embodiment of the 3D game of the present disclosure is described as follows. The player is a galactic soldier tasked with defending planet Earth from various space-insect enemies. The player will control the position of their "fire" crosshair (visually displayed as a difference of Gaussian/DOG) by their eyes (no joystick or mouse). A goal of this game is to help users manage convergence insufficiency by stimulating convergence with an emphasis on stimulating the preprogrammed component of disparity vergence and providing an alternate to tedious, eye exercises currently performed by users. This game is also meant to be entertaining for all users, and therefore provides an environment that provides entertainment and therapy together. In one embodiment of the 3D game, the eye movements of the user can direct missiles which they fire at incoming enemy ships in order to destroy them before they collide with the user's ship. Enemies spawn at various locations on the screen but move toward the midline axis while simultaneously approaching the user's first person field of vision. Different variations of the game can be easily programmed referred to as gaming 'skins.' The mechanics of the eye remain the same where the eye position is used to improve vergence performance but the visual environment and 3D models of the game change so that the user does not perceive he/she is actually performing repetitive eye movements.

Genre:

In this example embodiment of the present disclosure, the 3D game provides a 3D space shooter game. While this example embodiment utilizes a 3D space shooter game as a mechanism for visual therapy, exemplary embodiment of the present disclosure can implement different genres of games.

Target Audience:

Exemplary embodiments of the 3D game are developed for users suffering from binocular dysfunctions. However, the 3D game can be a fun and engaging form of entertainment for children between the ages of 8 and 18 and can also be used by adults of all ages and potentially children younger than 8 years depending on their skill sets.

Game Flow Summary:

The user/player will navigate through the game using only the movement of their eyes (e.g., the 3D game dynamically reacts to the player's detected eye movements). At certain points during menu selection, for example, the player may interact with other inputs, such as pressing one or more buttons on a keyboard.

Look and Feel:

The aesthetic direction of embodiments of the game can be a 3D, semi-cartoon, semi sci-fi art direction. The game can be developed so that the player feels excited throughout the game, and plays with a sort of epic zealousness. Embodiments of the games can include cut scenes and other details (music, action-sequences, etc. . . . ). Keep in mind that the fate of planet Earth is in the player's hands!

Gameplay and Mechanics

Game Progression:

Embodiments of the game can have various difficulty levels to support player progression through the game. Along with the player being able to control the difficulty of the game, various aspects of the game become more challenging as the game naturally progresses. For example, level 3 is more challenging than level 1. For example the threshold will be moved closer to the player; thus, the player has less time to respond to the enemies and less time to shoot them down.

Each "level" of the game can be broken down into sub-components. There is the "WARNING: INCOMING ENEMY SHIP APPROACHING" scene which serves to build anticipation, excitement, and set the mood for the coming battle. This same scene is always played first in the sequence of scenes described here. The next, the scene is where the parrot commander says a brief silly line or two to attract the attention of the younger players and to briefly give information about the incoming enemies. (The parrot may also give the player tips about how to do better in the game, or describe the difference between armored and non-armored enemies, for instance). A cut scene delineating the enemy fleet of ships then plays, in order to prepare the player for combat and engage the emotion of the player even further. After all of this suspense is built, the player will finally have the opportunity to engage the enemy in battle. This portion of the game is not only where the therapy takes place but also where the player's eye movements directly correlate to in-game performance. This part of the game is also going to be the longest, as player involvement and interactivity is what makes a game fun. Finally, the player will arrive at a screen that shows their performance in terms of accuracy percentage and damage taken to their ship, along with an overall grade/rating of how they performed in game. A "compliment" at the top of the screen to boost player moral (i.e. "Nice work" or "Great job"), and a comment from the parrot commander on their performance will be displayed. At this point, the parrot may give the player feedback that is in the form of tips on how to improve their gameplay strategy. The "bank" for this advice will fall under the category of artificial intelligence (AI) programming, and will be described in detail later in this documentation. The cycle of scenes is as follows:

WARNING ☐☐PARROT ADVICE ☐☐CUT SCENE ☐☐BATTLE ☐☐FEEDBACK SCENE ☐☐

The cycle then repeats itself throughout the rest of the game. Another element of progression not mentioned above is that the player earns an extra life after achieving a certain score.

In addition, the player will have access to a map of the game world which will track the locations they visit throughout the game. The player will be able to choose which sequence s/he wants to progress through the game.

Mission/Challenge Structure:

The "missions" is what the player will go through in the form of the game levels where the player is fighting enemies.

Puzzle Structure:

Puzzles may play in the overall game and may be a part of the therapeutic section of the game.

Objectives:

An objective of the game can be to obtain the highest score possible and also to defeat all of the enemies in each area of the game, ostensibly "beating" the game. More advanced players may, for example, decide that it is their objective to collect all of the weapons, in order to more thoroughly complete the game. For this reason amongst others, there can be inventory and save mechanisms built into the game.

Play Flow:

A sample gameplay session can proceed as follows:

1. The intro cut scene would play and introduce the player to the game. Alternately the introduction scene can be skipped if player wishes or could also be used a rest to the visual system especially for users with binocular dysfunctions.

2. The player can choose a destination on the map (out of the ones unlocked) to play.

3. The player can watch a brief intro cut scene to the level.

4. The player can then shoot at various enemies spawned from the mother ship until they reached a certain score/defeated all of the enemies.

5. The player can receive feedback of how s/he did on that level, which s/he would be able to send to the clinician.

6. The player can have the option (on the map) of going to a vendor to purchase various game components based on the amount of points they earned.

7. The cycle can then repeat, starting with the player choosing another location on the map to play.

The entertainment goal of this game is to evoke feelings of excitement, suspense, and flow in the player while allowing them to combat convergence insufficiency.

Mechanics

Physics:

Since the game takes place in outer space, the enemies are naturally floating around in a near-zero gravity atmosphere. Each of the collide-able game objects will have a rigid body component attached to it, as rigid bodies run off of Unity's native physics system. Unity is the computer language that embodiments of the 3D games can utilize.

Movement in the Game:

The missile firing system is controlled by the player's eye position. Navigation on the map screen and in the vendor scene either takes place through eye position or via input from the mouse. Changing weapons will take place by pressing the number keys, similar to Quake and other First Person Shooter (FPS) games.

Objects:

All objects in the game can be controlled by the user either moving or resting their eyes.

Actions:

As stated above, all actions take place via the position and activity performed by the user's eyes.

Combat:

During various parts of the game, the player is required to shoot "space bugs" in order to improve their score. Each space bug has an armored and non-armored version associated with its respective type. Armored versions can retreat behind the threshold point and therefore be more pestering than regular enemies. The player obtains various weapons to perform this combat, many of which will have to be "purchased" in game using their score points mentioned above.

Economy:

The player can use the points they earn by terminating bugs to purchase items in game, mainly weapons. The player obtain power ups by fixating on them during the same scenes as the bug combat, and maybe even in others as well (i.e. cut scene incentives).

Lens Analysis Through Jesse Schell's the Art of Game Design a Book of Lenses

1. The Lens of Essential Experience
   a. The player should have an experience with three main components:
      i. Controlling the game using their eyes; scientific and therapeutically challenging experience.
      ii. Epic sense of action and adventure as they fight to save planet earth from the evil insect hoards trying to obliterate it.
      iii. Fun and immersive gameplay that has strong replay value (the user will have to play the game many times during his/her therapy).
   b. Again this experience has to be analyzed from the three perspectives from which it is designed (therapeutic, cinematic, and immersive)
      i. Essential to the visual experience is allowing the player's eyes to control just about every aspect of the game.
      ii. Dramatic cut scenes and a compelling storyline that sets the stage for the player.
      iii. Challenges and incentives (i.e. digital awards) that keep the player coming back for more.
   c. The game can capture the sought after essence in each category in a number of ways:
      i. Integrated cameras in the Oculus rift to track eye position and resting eyes on a certain location to function as a mouse click or button press.
      ii. A kid-friendly storyline that engages the player in an epic quest to save planet earth. Achieved through cut scenes and other in-game cinematic elements.
      iii. The game needs to evolve in terms of development in a few ways: 1. Branching path storyline that gives the player more than one option (i.e. maybe the player can be the bad guy and fight against planet earth, etc. . . . )
   d. A save mechanism will be built into the game.
2. The Lens of Surprise
   a. Players will be surprised at the amount of ally forces that are shown in the storyline as they come in to defend planet earth. They should also be excited and surprised that they can control this game with their mind.
   b. The story has the main surprise of the evil forces assembling to fight the good forces. The threshold is a surprising twist to the game rules, as it makes it harder for the player but increases their score dramatically if used. There is a secret room on the ship which should also surprise players. The artwork will have some surprises. The main component of the technology that should surprise the player is the fact that the game will be played with the person's eye position.
   c. This is not a multiplayer game.
   d. Rules give players ways to surprise themselves in that testing out different weapons can have exciting and varying effects to enemies.
3. The lens of fun
   a. The integration of the player's name directly into the game makes it a more immersive experience for the player. In addition, the cinematic storyline components are crucial in catching and maintaining player interest. These make the game fun for the player because they immerse the player in an alternate virtual reality that is engaging and intriguing. 4. The Lens of Curiosity
   a. There are many questions that may arise in the player's mind regarding the game:
      i. Who are the ally characters and why do they want to save planet earth?
      ii. Why do the spider and his insect minions want to destroy planet earth?
      iii. Will they get to fight the spider?
      iv. What allies will rally behind them to fight for earth?
      v. How can I achieve the highest score possible in the game?
      vi. Are there hidden weapons/levels? b. The cinematic cut scenes make the player care about these questions by setting up a dramatic storyline for the player to follow and enjoy.
   c. A series of cinematic twists also embed player response cues into the core gameplay to obtain player feedback in the game.
5. The Lens of Endogenous Value
   a. The valuable items to players are the game score, the power-ups, and the weapons in the game.
   b. The player's motivation is to beat the game, i.e. defeat all of the enemies and enemy ships at the different levels of the game. The score allows players to unlock and purchase weapons and power ups, which make it easier for them to beat the game and accumulate a higher score.
6. The Lens of Problem Solving
   a. The game asks the player to converge their eyes when the enemies approach in order to fixate at the enemies and eliminate them.
   b. There is a hidden puzzle in the game that allows the player to obtain the threshold (i.e. morpher) which, ironically, assists their therapy even further.
   c. The game can have puzzle based levels where converging the player's eyes at a certain moment lets them unlock new things.
7. The Lens of the Elemental Tetrad
   a. The game incorporates aesthetics in the form of 3D models, interface design, etc. . . . . . In terms of the storyline, the game uses cinematic cut scenes and dramatic music to build emotion and player attachment to the game. The mechanics of the game tie together the therapeutic and gameplay objectives within the game.

One embodiment of the game uses an oculus rift (other head mounted displays can be used in the future) that has been modified to detect eye movement of a player, so it fulfills the technology component of the tetrad. The tracking of eye position helps to push the boundaries of the technology used for this game as well. Hence, embodiments of the games of present disclosure can use elements of all four types delineated in the tetrad model.

b. Adding more animations to the 3D models could improve the feel and design of the game, especially in the areas of cut scenes and gameplay effects.

c. The four elements are in harmony and working towards a common theme.

8. The Lens of Holographic Design
   a. The game elements that make the experience enjoyable are the compelling storyline, in which younger players are likely to form relationships with the characters, the assistance that these characters lend the player during levels in the game, and the space shooter style of gameplay being able to be controlled by the player's eye position.
   b. Improve the experience by making the enemies move in different formations and varying their height on the midline axis, so that the player does not become bored with monotonous repetition.

9. The Lens of Unification
   a. The theme of the game is that a group of extraterrestrial insect colonies are coming to earth to destroy our planet and the group of good animals, along with the player, must stop them from wiping out all of existence.

10. The Lens of Resonance
   a. The connections that the player makes to the non-player characters (npc) and the direct involvement of the player in the interactions in the game makes the player truly have a one-of-a-kind interactive game experience that can be controlled with their eyes.
   b. The fact that the game can be played using only a person's eye position further excites people about the game.

Enemy Spawns

Enemy Crosses Threshold

If user's gaze holds over enemy for certain length of time, weapon is fired.

If hit, enemy is destroyed.

Figure 9:
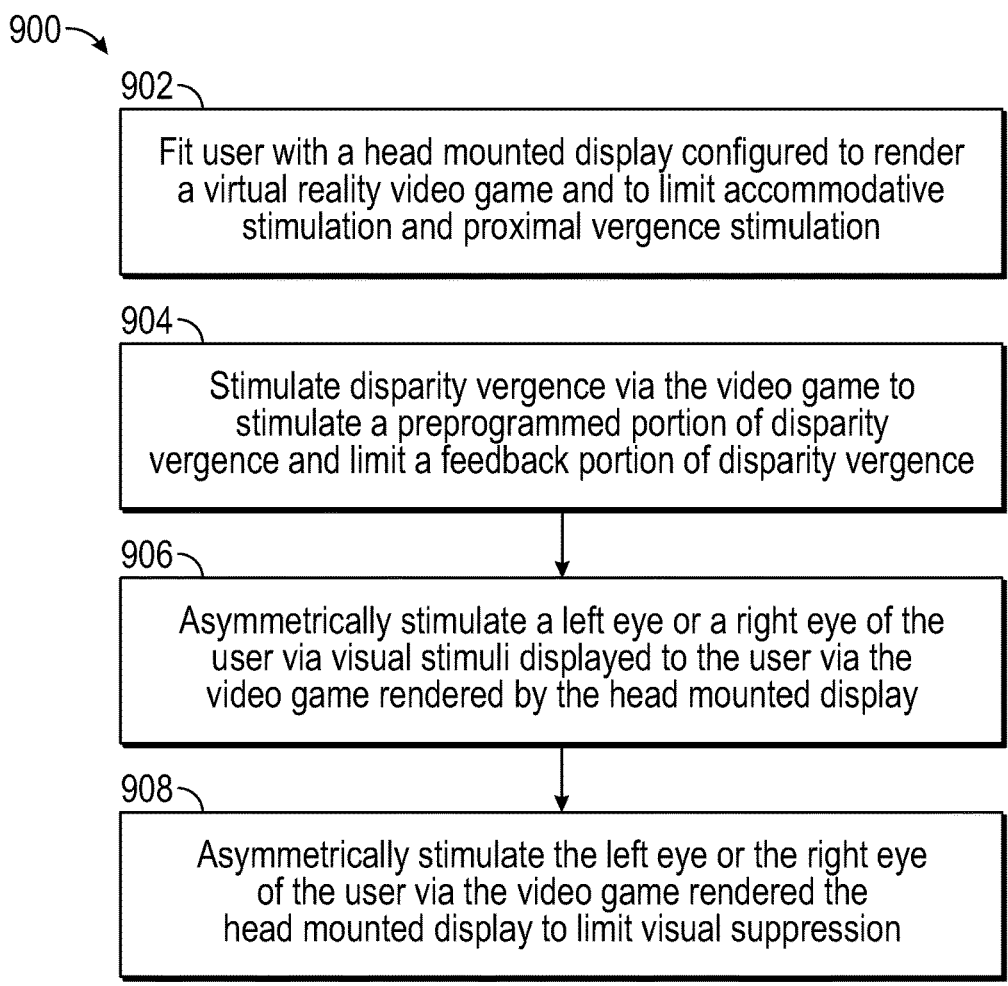
FIG. 9 is a flowchart illustrating an exemplary process for providing vision therapy for binocular dysfunction in accordance with embodiments of the present disclosure.

FIG. 9 is a flowchart illustrating an exemplary process 900 for providing vision therapy for binocular dysfunction in accordance with embodiments of the present disclosure. At step 902, a user is fitted with a head mounted display configured to render a virtual reality video game and to limit accommodative stimulation and proximal vergence stimulation. At step 904, disparity vergence is stimulated via the video game to stimulate a preprogrammed portion of disparity vergence and limit a feedback portion of disparity vergence. At step 906, a left eye or a right eye of the user is asymmetrically stimulated via visual stimuli displayed to the user via the video game rendered by the head mounted display. The left eye and the right eye can be asymmetrically stimulated based on an asymmetrical peak velocity difference between the left and right eyes. At step 908, the left eye or the right eye of the user is asymmetrically stimulated via the video game rendered by the head mounted display to limit visual suppression.

Figure 10:
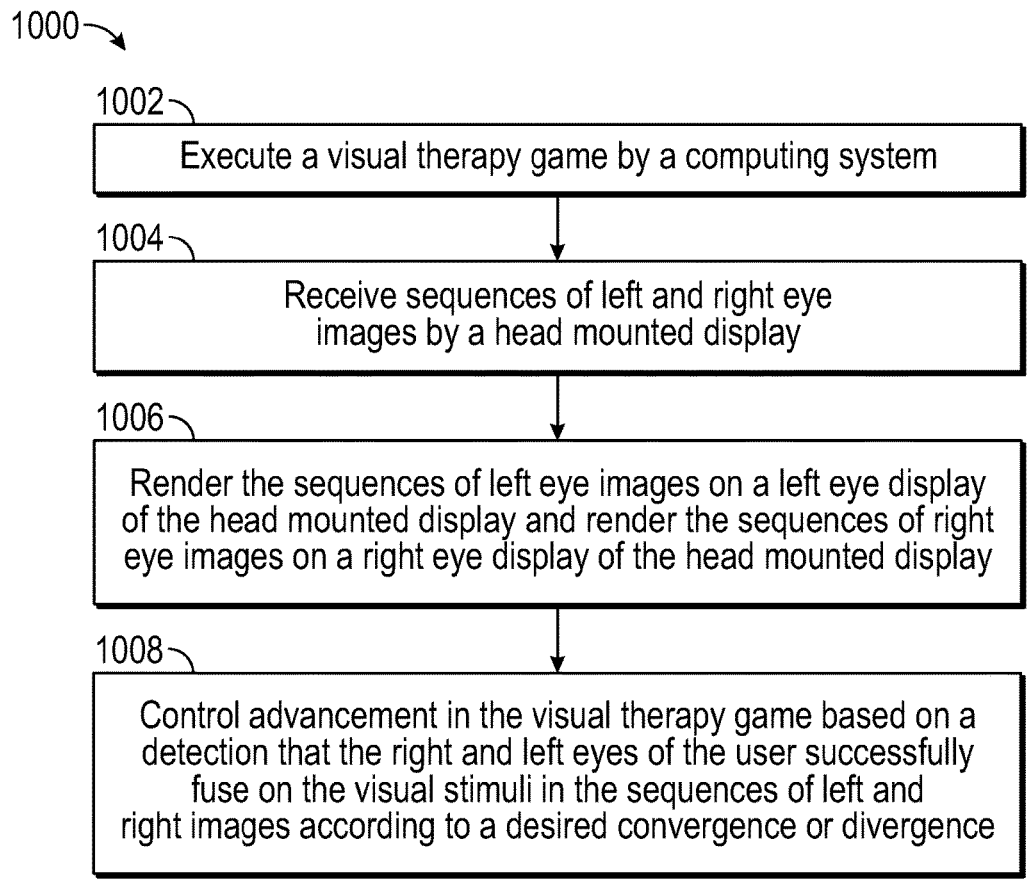
FIG. 10 is a flowchart illustrating an exemplary process for providing vision therapy for binocular dysfunction in accordance with embodiments of the present disclosure.

FIG. 10 is a flowchart illustrating an exemplary process 1000 for providing vision therapy for binocular dysfunction in accordance with embodiments of the present disclosure. At step 1002, a visual therapy game is executed by a computing system. At step 1004, sequences of left and right eye images are received by a head mounted display from the computing system in response to execution of the visual therapy game. The head mounted display is configured to be worn by a user and the left and right eye images include one or more visual stimuli. At steps 1006, the sequences of left eye images are rendered on a left eye display of the head mounted display and the sequences of right eye images are rendered on a right eye display of the head mounted display. A (first) focal length between a left eye of the user and the left eye display is fixed and a (second) focal length between the right eye of the user and the right eye display being fixed. At step 1008, advancement in the visual therapy game is controlled based on a detection that the right and left eyes of the user fuses on the visual stimuli in the sequences of left and right images according to a desired convergence or divergence.

Figure 11:
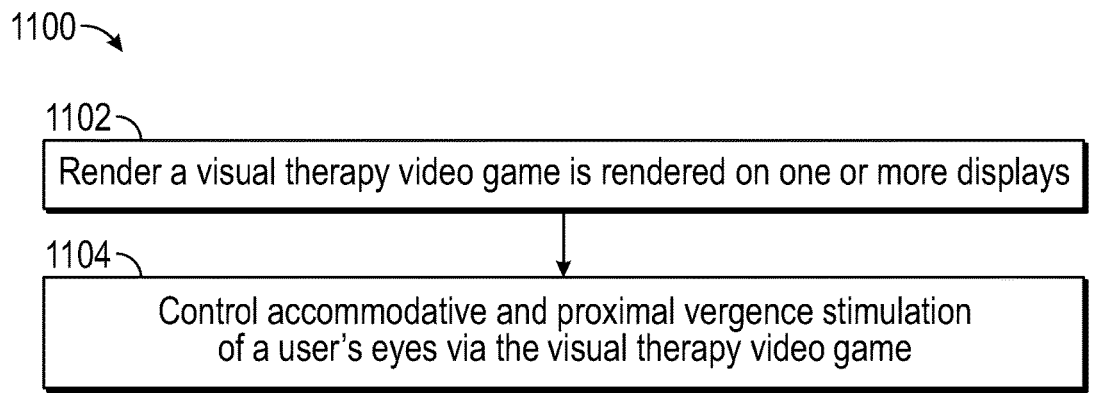
FIG. 11 is an exemplary process for remediating visual symptoms in a user with a binocular dysfunction in accordance with embodiments of the present disclosure.

FIG. 11 is a flowchart illustrating an exemplary process 1100 for remediating visual symptoms in a user with a binocular dysfunction in accordance with embodiments of the present disclosure. At step 1102, a visual therapy video game is rendered on one or more displays. At step 1104, accommodative and proximal vergence stimulation of a user's eyes is controlled via the visual therapy video game.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

The invention claimed is:

1. A method for remediating visual symptoms in a user with binocular dysfunction, the method comprising:
   rendering a visual therapy video game on one or more displays;
   controlling accommodative and proximal vergence stimulation of a user's eyes via the visual therapy video game; and
   asymmetrical stimulating to a left eye or a right eye of the user via the visual therapy video game based on peak velocity differences between the left and right eyes.

2. The method of claim 1, wherein the visual therapy video game is rendered by a head mounted display with integrated eye tracking hardware and software.

3. The method of claim 1, further comprising: stimulating a preprogrammed portion of disparity vergence; and limiting a feedback portion of disparity vergence.

4. The method of claim 1, wherein a magnitude of asymmetrical stimulation is derived from a position of the left and right eyes.

5. The method of claim 4, wherein the magnitude of asymmetrical stimulation dynamically changes to limit visual suppression.

6. The method of claim 1, wherein the visual therapy video game is a virtual reality video game.

7. The method of claim 6, further comprising: detecting real-time physical eye movements of the left and right eyes of the user; and using the real-time physical eye movements of the left and right eyes of the user as inputs for the visual therapy video game.

8. The method of claim 7, further comprising: determining a point in a three-dimensional virtual reality space to which the user's left and right eyes are fused based on the real-time physical eye movements.

9. The method of claim 6, wherein the visual therapy video game includes one or more visual cues to limit accommodative stimulation.

10. A method for treating binocular dysfunction comprising:
fitting a user with a head mounted display configured to render a virtual reality video game and to limit accommodative stimulation and proximal vergence stimulation;
stimulating disparity vergence via the virtual reality video game to stimulate a preprogrammed portion of disparity vergence and limit a feedback portion of disparity vergence;
asymmetrically stimulating a left eye and a right eye of the user via visual stimuli displayed by the virtual reality video game rendered by the head mounted display, the left eye and the right eye being asymmetrically stimulated based on an asymmetrical peak velocity difference between the left and right eyes; and
asymmetrically stimulating the left eye and the right eye of the user via the virtual reality video game rendered by the head mounted display to limit visual suppression.

11. The method of claim 10, wherein the head mounted display includes a right eye display and a left eye display configured to render the virtual reality video game and includes a right eye image capturing device disposed proximate to the right eye display and a left eye image capturing device disposed proximate to the left eye image capturing device, and the method further comprises:
determining the asymmetrical peak velocity difference between the left and right eyes based in images of the left and right eyes captured by the left and right image capturing devices and the left and right eyes move in response to viewing the left and right eye displays.

12. The method of claim 11, wherein a focal length between the right eye and the right eye display is fixed when the head mounted display is fitted to the user's head.

13. The method of claim 11, further comprising: dynamically adjusting a magnitude of the asymmetrical stimulation in the virtual reality video game to limit visual suppression.

14. The method of claim 10, wherein the virtual reality video game is render stereoscopically to render the virtual reality video game in three-dimensional virtual space.

15. A system for remediating visual symptoms in a user with binocular dysfunction, the system comprising:
a computing system configured to execute a visual therapy video game; and
a head mounted display operatively coupled to the computing system, the head mounted display including:
a first display for the left eye;
a second display for the right eye; one or more display controllers configured to render images on the first display and the second display of the head mounted display to generate a stereoscopic effect;
a first image capturing device disposed proximate to the first display, the first image capturing device being configured to capture images of a left eye of a user of the head mounted display; and
a second image capturing device disposed proximate to the second display, the second image capturing device being configured to capture images of a right eye of the user,
wherein the computing system outputs the visual therapy video game to the head mounted display, the head mounted display outputs positions of the right and left eyes based on the images captured by the first and second image capturing devices, and the computing system controls the visual therapy video game based on the positions of the right and left eyes,
wherein advancement in the visual therapy video game is controlled based on a detection that the left and right eyes of the user fuse on visual stimuli in the visual therapy video game,
wherein in response to execution of the visual therapy video game by the computing system, the first display or the second display render the visual therapy video game to asymmetrically stimulate the left eye and the right eye of the user via the visual therapy video game based on peak velocity differences between the left and right eyes.

16. The system of claim 15, wherein the first and second displays render the visual therapy video game to stimulate a preprogrammed portion of disparity vergence and limit a feedback portion of disparity vergence.

17. The system of claim 15, wherein in response to execution of the visual therapy video game by the computing system, the first display or the second display render the visual therapy video game to asymmetrically stimulate the left eye and the right eye of the user.

18. The system of claim 15, wherein a magnitude of asymmetrical stimulation is derived from a position of the left and right eyes.

* * * * *